United States Patent
Seidl (10) Patent No.: US 7,298,788 B2
(45) Date of Patent: Nov. 20, 2007

(54) WIRELESS COMMUNICATION SYSTEM AND METHOD

(75) Inventor: Neal J. Seidl, New Berlin, WI (US)

(73) Assignee: GE Medical Systems Information Technologies, Inc., Waukesha, WI (US)

( * ) Notice: Subject to any disclaimer, the term of this patent is extended or adjusted under 35 U.S.C. 154(b) by 778 days.

(21) Appl. No.: 10/694,039

(22) Filed: Oct. 27, 2003

(65) Prior Publication Data

US 2005/0089113 A1    Apr. 28, 2005

(51) Int. Cl.
*H04L 27/10* (2006.01)
*H03D 3/00* (2006.01)

(52) U.S. Cl. ...................... 375/272; 375/334

(58) Field of Classification Search ............. 375/272, 375/279, 283, 329, 334, 130, 303; 455/151.2
See application file for complete search history.

(56) References Cited

U.S. PATENT DOCUMENTS

| | | | | |
|---|---|---|---|---|
| 4,628,507 | A * | 12/1986 | Otani | 714/705 |
| 5,805,018 | A * | 9/1998 | Harima | 329/304 |
| 2002/0118780 | A1 | 8/2002 | Hurley et al. | |
| 2002/0194567 | A1* | 12/2002 | Yellin et al. | 714/758 |
| 2004/0128608 | A1* | 7/2004 | Kim et al. | 714/763 |

OTHER PUBLICATIONS

U.S. Appl. No. 10/704,430, filed Nov. 7, 2003, Carvalho et al.
D.R. Pauluzzi and N.C. Beaulieu, "A Comparison of SNR Estimation Techniques for the AWGN Channel," *IEEE Transactions on Communications*, vol. 48, No. 10, pp. 1681-1691, Oct. 2000.
T.R. Benedict and T.T. Soong, "The joint estimation of signal and noise from the sum envelope," *IEEE Trans. Information Theory*, vol. IT-13, pp. 447-454, Jul. 1967.
P.J. Bickel and K.A. Doksum, *Mathematical Statistics*, Holden-Day, 1977.
V.K. Rohatgi, *An Introduction to Probability Theory and Mathematical Statistics*, John Wiley and Sons, 1976.
Murota, K. and Hirade, K. "GMSK Modulation for Digital Mobile Radio Telephony," IEEE Transaction on Communications, vol. COM-29, pp. 1044-1050, No. 7, Jul. 1981.
Pasupathy, S., "Minimum Shift Keying: A Spectrally Efficient Modulation," IEEE Communications Magazine, vol. 0163-6804/79/0700-0014, Jul. 1979.
Elnoubi, S.M. "Analysis of GMSK with Differential Detection in Land Mobile Radio Channels," IEEE Transactions on Vehicular Technology, vol. VT-35, No. 4, Nov. 1986.

(Continued)

*Primary Examiner*—Khai Tran
(74) *Attorney, Agent, or Firm*—Andrus, Sceales, Starke & Sawall, LLP (57) ABSTRACT

A communication system including a first device transmitting a modulated signal and a second device receiving the modulated signal. The second device can include a first demodulator and a second demodulator. The first demodulator can receive the modulated signal, produce a first demodulated output, and implement a first demodulation technique. The second demodulator can receive the modulated signal, produce a second demodulated output, and implement a second demodulation technique. The second demodulation technique can differ from the first demodulation technique. The second device can also include an error detection module that can perform bit error detection based on the first demodulated output and the second demodulated output.

12 Claims, 10 Drawing Sheets

OTHER PUBLICATIONS

R. de Buda, "Coherent demodulation of frequency-shift keying with low deviation ratio," IEEE *Trans. Communications*, vol. COM-20, pp. 429-435, Jun. 1972.

P. Galko and S. Pasupathy, "Linear receivers for correlatively coded MSK," *IEEE Trans. Communications*, vol. COM-33, Apr. 1985, pp. 338-347.

G.K. Kaleh, "Simple coherent receivers for partial response continuous phase modulation," *IEEE Journal on Selected Areas of Communication*, vol. SAC-7, Dec. 1989.

P. Laurent, "Exact and approximate construction of digital phase modulations by superposition of amplitude modulated pulses," IEEE *Trans. Communications*, vol. COM-34, pp. 150-160, Feb. 1986.

N. Al-Dhahir and G. Saulnier, "A high-performance reduced-complexity GMSK demodulator," IEEE *Trans. Communications*, vol. 46, pp. 1409-1412, Nov. 1998.

F. Amoroso and J.A. Kivett, "Simplified MSK signaling technique," IEEE *Trans. Communications*, vol. COM-25, pp. 433-441, Apr. 1977.

W.P. Osborne and M.B. Luntz, "Coherent and NonCoherent Detection of CPFSK," *IEEE Trans. Communications*, vol. COM-22, pp. 1023-1036, Aug. 1974.

M.S. Hodgart and J.A. Schoonees, "A robust MSK demodulator through DSP," *Proc. IEEE 1992 S. African Symposium on Communications and Signal Processing*, Sep. 1992.

K.H. Mueller and M.S. Muller, "Timing recovery in digital synchronous data receivers," IEEE Trans. Communications, vol. COM-24, pp. 516-531, May 1976.

T.I. Laakso, V. Valimaki, M. Karjalainen and U.K. Laine, "Splitting the unit delay," IEEE *Signal Processing Magazine*, vol. 13, pp. 30-60, Jan. 1996.

* cited by examiner

WIRELESS COMMUNICATION SYSTEM AND METHOD

BACKGROUND OF THE INVENTION

The present invention relates to wireless communication systems, and, more specifically to wireless communication systems using various modulation techniques.

Gaussian minimum shift keying ("GMSK") is a popular modulation technique due to its simplicity and bandwidth efficiency. A popular technique for generating GMSK signals is "direct modulation" in which the modulation is performed directly in the frequency synthesizer. However, one drawback of direct modulation is that it is difficult to maintain adequate control over the modulation index and the filter bandwidth because of variations in the analog circuitry and the effects of tuning the synthesizer to different center frequencies. Designing a transmitter that can maintain a near-ideal minimum shift keying ("MSK") modulation index (e.g., by generating the baseband modulation in a digital signal processor) generally results in additional cost, complexity and power consumption. Thus, a demodulator for which performance is insensitive to modulation index is desired.

SUMMARY OF THE INVENTION

In one embodiment, the invention provides a communication system that can include a first device transmitting a modulated signal and a second device receiving the modulated signal. The second device can include a first demodulator, a second demodulator and an error detection module. The first demodulator can receive the modulated signal, produce a first demodulated output, and implement a first demodulation technique. The second demodulator can receive the modulated signal, produce a second demodulated output, and implement a second demodulation technique that is different from the first demodulation technique. The error detection module can perform bit error detection based on the first demodulated output and the second demodulated output.

In another embodiment, the invention provides a method of transferring information via radio frequency. The method can include converting information to a digital signal, modulating the digital signal to a modulated signal using a packetized protocol, and wirelessly transferring the modulated signal. The method can also include receiving the modulated signal, demodulating the modulated signal to produce a demodulated signal, and implementing an error detection algorithm.

In yet another embodiment, the invention provides a method for performing estimations of modulation signal parameters upon reception of a transmitted signal. The method can include demodulating the transmitted signal to produce a digital signal having a plurality of bits, storing the plurality of bits in an array, determining if the array contains a first pattern of bits or a second pattern of bits, and performing a modulation signal parameter estimation if the array contains a first pattern of bits or a second pattern of bits.

In a further embodiment, the invention provides a method of adapting the output of an equalizer in a communication system. The method can include receiving an input signal, determining a first output value during a first time interval of the input signal and determining a second output value during a second time interval of the input signal based in part on the first output value determined during the first time interval. The first time interval can precede the second time interval.

In yet a further embodiment, the invention provides a method of estimating the carrier offset of a modulated signal. The method can include receiving a input signal having a first input value during a first time interval and a second input value during a second time interval, receiving a first estimated parameter of the input signal and receiving a second estimated parameter of the input signal. The method can also include calculating an estimated signal during the second time interval, combining the second input value of the input signal with the estimated signal to produce an error signal and determining the carrier offset during the second time interval based in part on the error signal. The estimated signal may be a substantially noiseless estimation of the second input value during the second time interval of the input signal, and the estimated signal may be based in part on the first input value of the input signal, the first estimated parameter and the second estimated parameter.

Other features and advantages of the invention will become apparent to those of ordinary skill in the art upon review of the following description, claims and drawings.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limited. The use of "including," "comprising" or "having" and variations thereof herein is meant to encompass the items listed thereafter and equivalents thereof as well as additional items. The terms "mounted," "connected" and "coupled" are used broadly and encompass both direct and indirect mounting, connecting and coupling. Further, "connected" and "coupled" are not restricted to physical or mechanical connections or couplings.

In addition, it should be understood that embodiments of the invention include both hardware and electronic components or modules that, for purposes of discussion, may be illustrated and described as if the majority of the components were implemented solely in hardware. However, one of ordinary skill in the art, and based on a reading of this detailed description, would recognize that, in at least one embodiment, the electronic based aspects of the invention may be implemented in software. As such, it should be noted that a plurality of hardware and software based devices, as well as a plurality of different structural components may be utilized to implement the invention. Furthermore, and as described in subsequent paragraphs, the specific mechanical configurations illustrated in the drawings are intended to exemplify embodiments of the invention and that other alternative mechanical configurations are possible.

Figure 1:
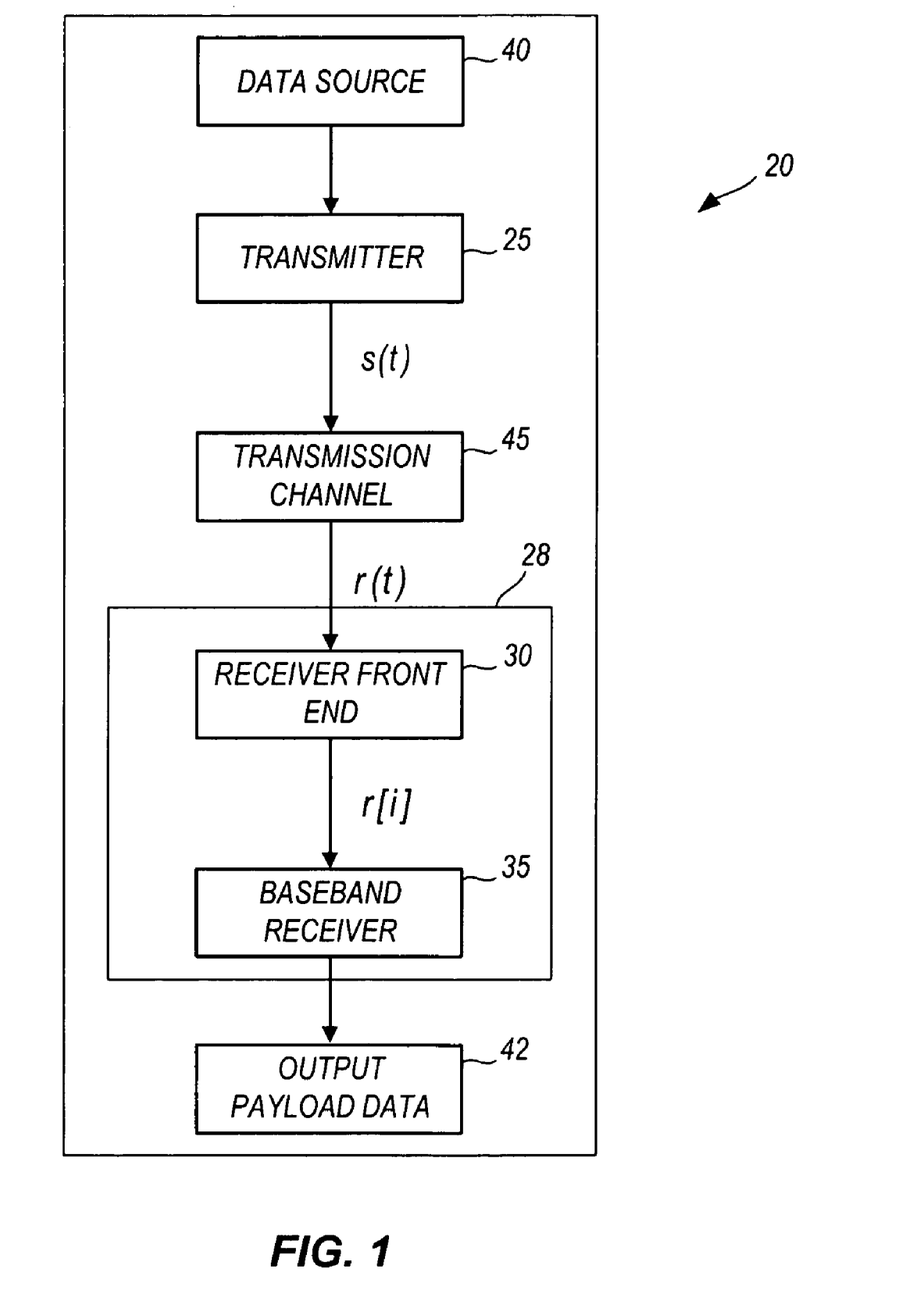
FIG. 1 is a schematic diagram of a communication system embodying the invention.

FIG. 1 illustrates a communication system 20 according to one embodiment of the invention. The communication system 20 includes a transmitter 25 and a receiver 28. The receiver 28 can include a receiver front-end 30 and a baseband receiver 35. The transmitter 25 receives payload data (e.g., data to be transmitted) from a data source 40. The transmitter 25 modulates the payload data with a modulation technique [e.g., minimum shift keying ("MSK") modulation, Gaussian minimum shift keying ("GMSK") modulation, frequency shift keying ("FSK") modulation, differential frequency shift keying ("differential FSK") modulation, or Gaussian frequency shift keying ("GFSK") modulation], and transmits the modulated signal to the receiver 28.

In one embodiment, the transmitter 25 can encode payload data according to a packetized protocol or packet-orientated protocol and can modulate the resulting bit stream using GFSK modulation to produce the modulated signal s(t). In an exemplary implementation, the transmitter 25 acquires ECG data, which can be filtered and transmitted to the receiver 28 at a rate of approximately 120-samples per second. The transmitter 25 sends the data out at a rate of approximately 10-Kbps in a protocol which specifies 125-packets per second. Each packet of data can contain one of the 120-Hz samples acquired by the transmitter 25. This may result in only 120 of the 125 packets per second contain the acquired ECG data and that the remaining packets may not contain any data. In one exemplary implementation, the remaining five packets do not contain any data and are referred to as "blank packets." Blank packets may have unique identifiers, may be grouped together in time and may be periodic.

In one embodiment, the packetized protocol organizes data to be transmitted per second into 120 packets, labeling the first data packet as data packet 0 ("DP0") and the last data packet as data packet 119 ("DP119"). The data packets in between data packet DP0 and DP119 are labeled accordingly. Data packets DP0 through DP119 are arranged in sequential and consecutive order. A series of five consecutive blank data packets [blank packet 0 ("BP0") through blank packet 4 ("BP4")] are positioned after the last data packet DP119 in the modulated signal s(t). The burst of five blank data packets BP0 through BP4 occur once per second. In other embodiments, the total number of data packets and/or blank packets differ from the first embodiment and/or the packetized protocol may organize the data into a different pattern of data packets and blank packets.

In one embodiment, the receiver 28 can receive the first blank packet BP0 and can estimate the time period until the next group of blank packets. In general, estimation of the time period or required interval, as opposed to certain knowledge of that interval, is considered because of pipeline delays in the receiver, the values of which need not be constant. After the estimated time period elapses, the receiver 28 may stop demodulating the incoming signal and perform system calculations, such as, for example, switching through all of the antenna fields if applicable and estimating the signal power for each. In some embodiments, the packetized protocol allows the receiver 28 to implement a method of error detection and correction through the use of parallel demodulators, as will be discussed below.

As shown in FIG. 1, the modulated signal s(t) can be transmitted through a transmission channel 45 where the signal s(t) is attenuated and corrupted by additive noise. In one embodiment, the receiver front-end 30 can receive the attenuated and corrupted modulated signal, now the received signal r(t), and can amplify the received signal r(t). In one embodiment, the received signal r(t) is down-converted to baseband in-phase and quadrature components after the signal r(t) is amplified. These baseband components can be digitized and resampled synchronous to the bit stream to yield a discrete-time complex baseband signal r[i].

As shown in FIG. 1, the receiver front-end 30 can output the baseband signal r[i] to the baseband receiver 35. The baseband receiver 35 can demodulate the baseband signal r[i] to produce the output payload data 42. In some embodiments, the baseband receiver 35 can perform various and multiple demodulation techniques in order to produce the output payload data 42, which can be the payload data acquired from a data source 40 and transmitted by the transmitter 25.

Figure 2:
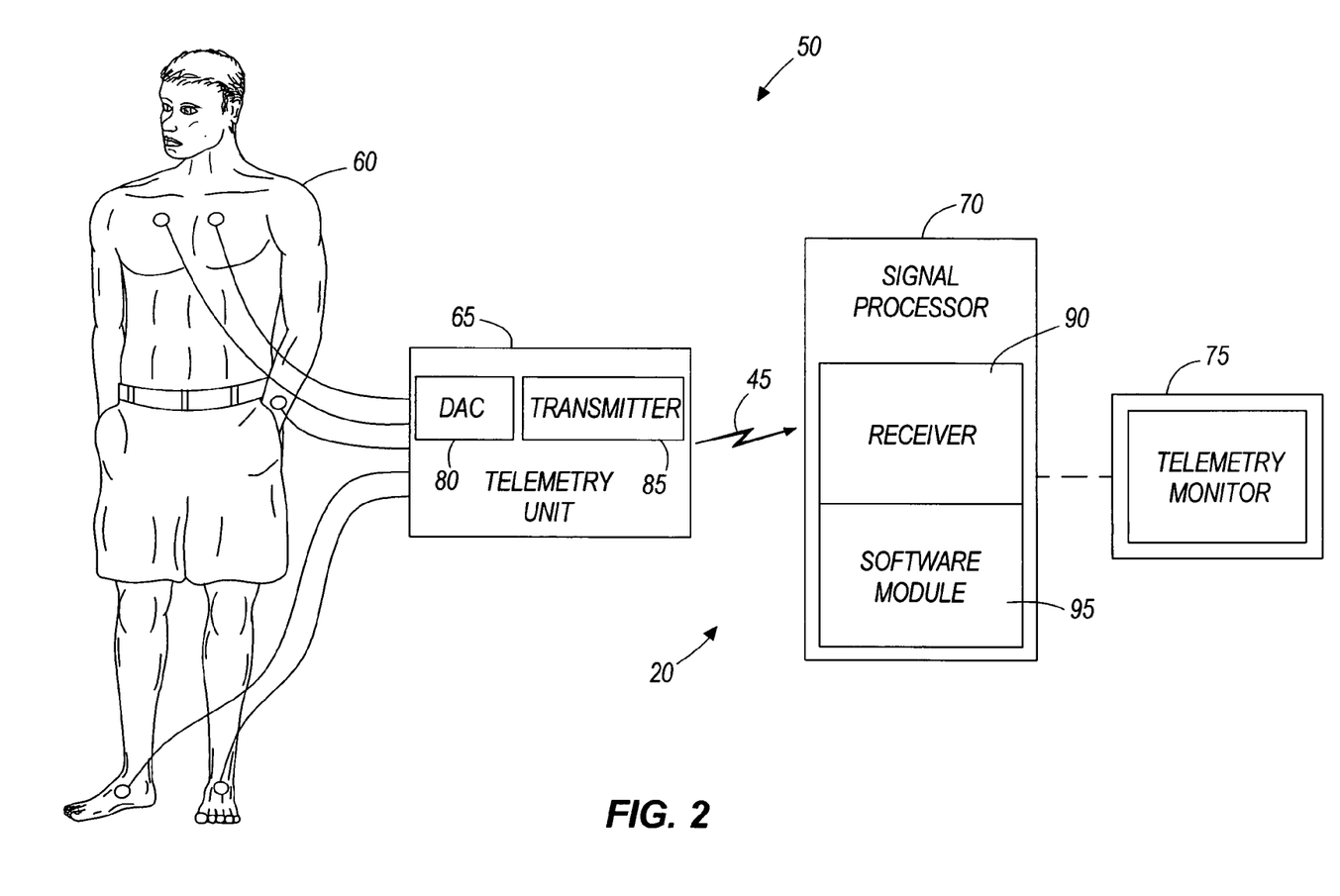
FIG. 2 is a schematic diagram of a telemetry system including the communication system of FIG. 1.

The communication system 20 can be used in a number of wireless communication applications and systems, such as, for example, telemetry systems, cellular telephone systems, satellite transmissions, etc. In one embodiment, as shown in FIG. 2, the communication system 20 is included in a telemetry system 50. The telemetry system 50 includes a telemetry unit 65 that acquires and monitors patient data from an ambulatory patient 60. In this embodiment, payload data is the data acquired from the patient. The telemetry unit 65 can transfer the acquired patient data to a signal processor 70 and/or a telemetry monitor 75.

As shown in FIG. 2, the telemetry unit 65 can include a data acquisition module ("DAC") 80 and a transmitter 85. The transmitter 85 can employ the various modulation techniques employed by the transmitter 25 described above with respect to FIG. 1. In some embodiments, the data acquisition module 80 receives and processes input patient data, such as ECG signals and/or blood pressure signals. In some embodiments, the data acquisition module 80 conditions the input patient data into a desired signal or readable output which is transmitted to the signal processor 70 by the transmitter 85. In other embodiments, the transmitter 85 conditions the input patient data acquired by the data acquisition module 80 and modulates the data into the modulated signal s(t) (as referred to in FIG. 1). The transmitter 85 can transmit the modulated signal s(t) over a transmission channel 45. In one embodiment, the transmitter 85 uses the GFSK modulation technique, and the transmission channel 45 operates in a frequency range of approximately 560 MHz to approximately 614 MHz. In some embodiments, the transmission channel 45 operates in additional or alternative frequency ranges, such as, for example, a frequency range of approximately 420 MHz to approximately 474 MHz and/or the range of approximately 190 MHz to approximately 220 MHz. The transmission channel 45 can also operate in a frequency range specified by various international regulations.

As shown in FIG. 2, the signal processor 70 includes a receiver 90, and a software module 95. The receiver 90 is an alternative embodiment of the receiver 28 as shown and described with respect to FIG. 1. The software module 95 can provide the necessary instructions for conditioning the received signal r(t) (as referred to in FIG. 1) and to perform any additional functions for the signal processor 70. In some embodiments, the software module 95 provides similar demodulation techniques and/or functions to demodulate and/or process the received signal r(t) as described above with respect to the baseband receiver 35.

Figure 3:
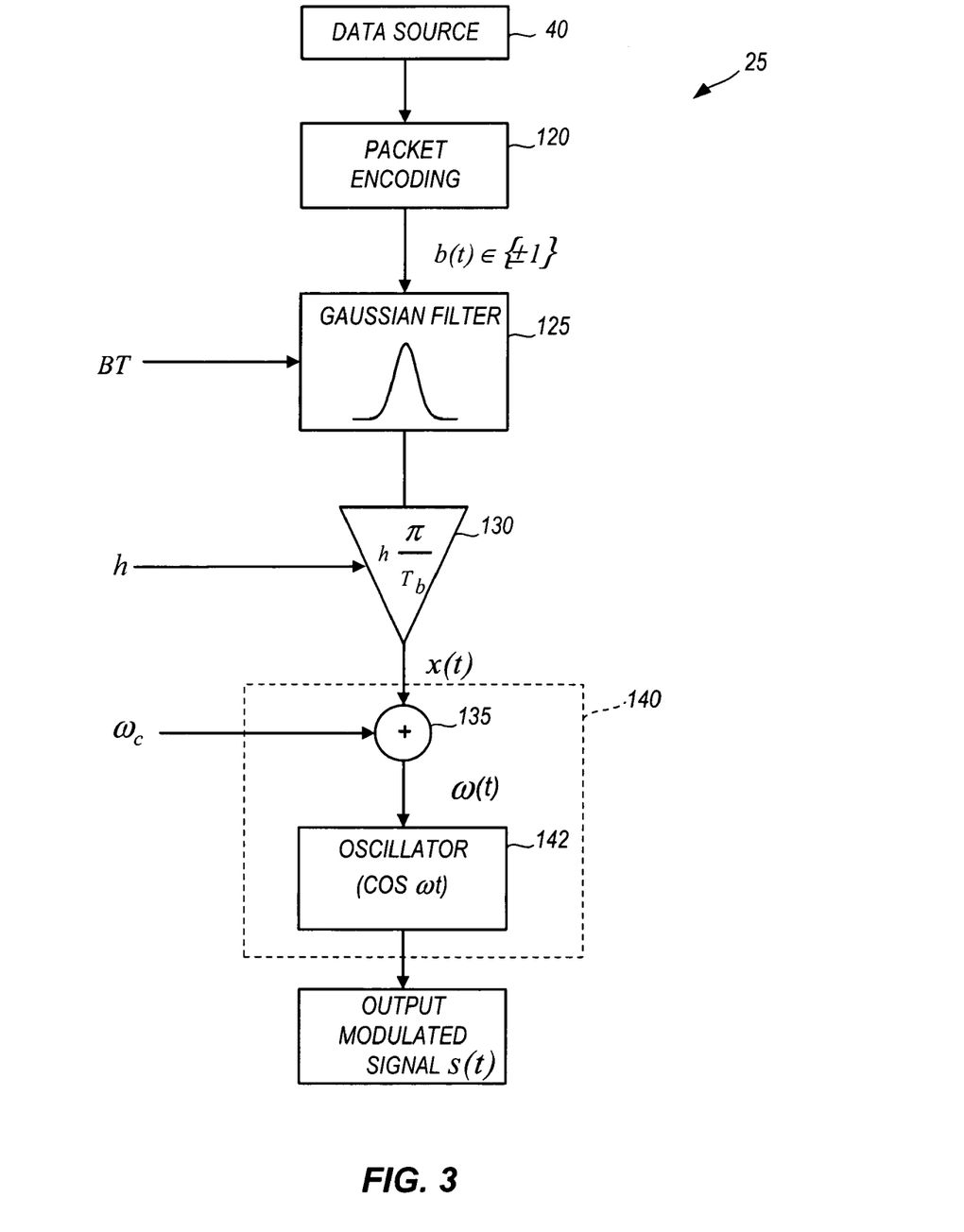
FIG. 3 is a schematic diagram of a transmitter included in the communication system of FIG. 1.

FIG. 3 illustrates one embodiment of the transmitter 25 and/or the transmitter 85. Payload data acquired from a data source 40 can pass through an encoder 120. The data can be encoded according to a packet-oriented protocol wherein each packet incorporates an error correcting code ("ECC"). The resulting bit stream can be output as a continuous-time rectangular waveform $b(t) \in \{\pm 1\}$. The waveform b(t) can then be filtered by a filter 125 (e.g., a Gaussian filter) and can be subjected to a gain by a gain module 130 (e.g., an amplifier or filter). The gain applied by the gain module 130 determines the modulation index h of the resulting modulating waveform x(t). In one embodiment, the gain of the gain module 130 is chosen to produce a non-MSK modulation index h (i.e., a modulation index h of approximately 0.6).

A modulator 140 receives the waveform x(t) and outputs the modulated signal s(t). The modulator 140 includes a combiner 135 and an oscillator 142. The waveform x(t) can then be used to modulate the frequency of a carrier signal with center frequency $\omega_c$ at the combiner 135. The output of the combiner 135 is the instantaneous frequency ω(t), which can pass through the oscillator 142. The FM transmitter 25 can include any suitable hardware and/or software components.

Figure 4:
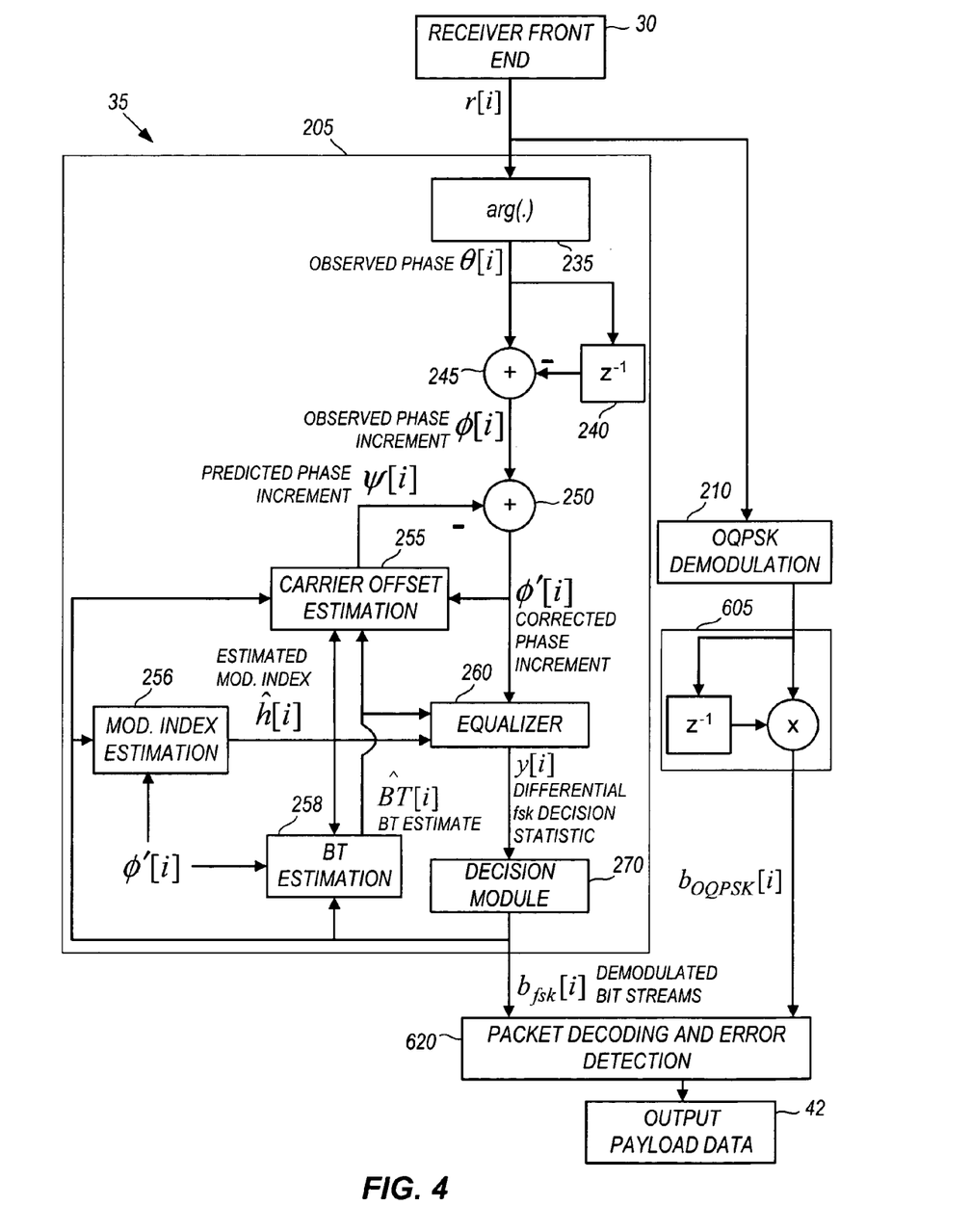
FIG. 4 is a schematic diagram of a baseband receiver included in the communication system of FIG. 1.

FIG. 4 illustrates one embodiment of the baseband receiver 35. The baseband receiver 35 can include a first demodulator 205 using a first demodulation technique and a second demodulator 210 using a second demodulation technique that differs from the first technique. As shown in FIG. 4, the first demodulator 205 uses an FSK demodulation technique and the second demodulator 210 uses an offset-quadrature phase shift keying ("OQPSK") demodulation technique. The second demodulator 210 can include any suitable hardware and/or software components. In other embodiments, the baseband receiver 35 can include more demodulators than the illustrated embodiments and can include other demodulation techniques than shown and described in the illustrated embodiments.

The receiver front-end 30 can output the discrete-time complex signal r[i] to the baseband receiver 35 for demodulation by the first and second demodulators 205 and 210. Upon input from the front-end receiver 30, the first demodulator 205 (i.e., the FSK demodulator) can extract the instantaneous observed phase θ[i] from the discrete-time complex baseband signal r[i] for each bit interval using phase module 235 [i.e., arg(.)]. The observed phase increment φ[i] can be computed as the first-difference of the instantaneous phase θ[i] by passing the instantaneous phase θ[i−1] through a sample delay (e.g., a 1-sample delay 240) to a combiner 245 where the instantaneous phase θ[i] (delayed by the 1-sample delay 240) is subtracted from the subsequent instantaneous phase θ[i]. The resulting observed phase increment φ[i] can pass through a second combiner 250 where the observed phase increment φ[i] can be combined with the predicted phase increment or correction phase ψ[i] (due to a constant carrier frequency offset of the transmitter 25 with respect to the center frequency tuned by the receiver 28). The second combiner 250 can produce an corrected phase increment φ'[i]. As shown in FIG. 4, the correction phase ψ[i] can be subtracted from the observed phase increment φ[i] to obtain the corrected phase increment φ'[i].

Figure 5:
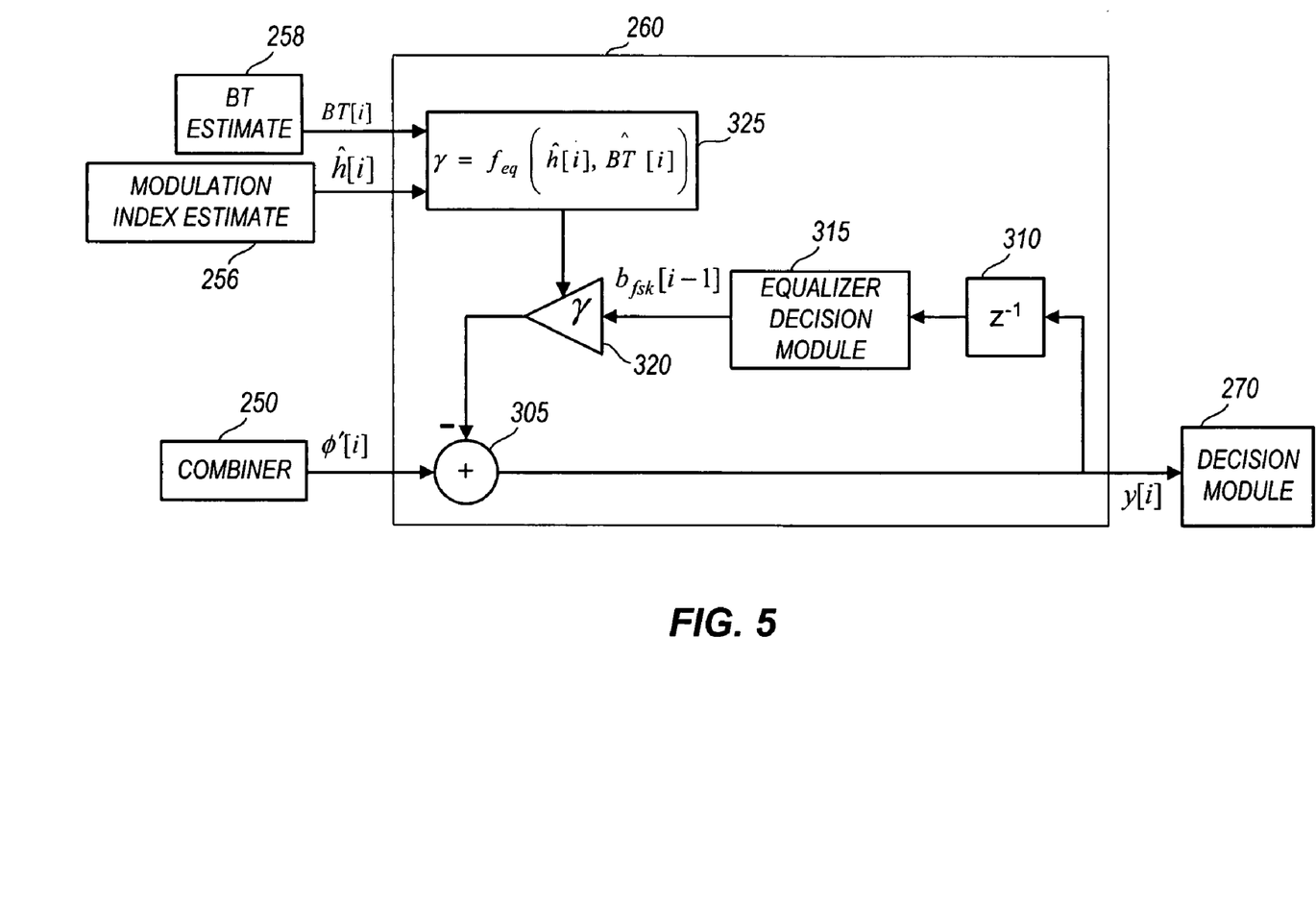
FIG. 5 is a schematic diagram of an adaptive non-linear equalizer included in the receiver of FIG. 4.

As shown in FIG. 4, the corrected phase increment φ'[i] can be used in various signal parameter estimation modules (e.g., a carrier offset estimation module 255, a modulation index estimation module 256 and a bandwidth-bit-duration estimation module 258). Every time step or interval, the corrected phase increment φ'[i] can proceed to an equalizer 260. The equalizer 260 can be an adaptive non-linear equalizer as shown in FIG. 5 according to one embodiment. The equalizer 260 can be applied to the corrected phase increment φ'[i] to obtain the equalized or differential FSK decision statistic y[i]. The adaptive equalizer 260 can receive various signal parameters to yield the equalized decision statistic y[i]. The adaptive equalizer 260 can base its output on the incoming corrected phase increment φ'[i], an estimated filter bandwidth-bit-duration parameter BT[i] and an estimated modulation index parameter h[i]. The decision module 270 can apply a decision rule (e.g., the signum function) to the equalized decision statistic y[i] as determined by the equalizer 260 to yield a final bit stream $b_{fsk}[i] \in \{\pm 1\}$.

As shown in FIG. 4, the first demodulator 205 can include a carrier offset estimation module 255, a modulation index estimation module 256, and a bandwidth-bit-duration estimation module 258. The carrier offset estimation module 255 can provide an estimate of the carrier offset ψ. The modulation index estimation module 256 can provide an estimate of the modulation index h, and the bandwidth-bit-duration estimation module 258 can provide an estimate of the filter bandwidth BT. In some embodiments, the carrier offset estimation module 255, the modulation index estimation module 256 and the bandwidth-bit-duration estimation module 258 can be used internally by the receivers 28 and 90 and can be used for system diagnostic purposes. The estimations provided by the estimation modules 255, 256 and 258 can be trended, reported and/or displayed over a predetermined time period. An out-of-range parameter or estimation may indicate a fault and may trigger an analysis of the transmitter 25 and localize hardware errors of the transmitter 25.

Figure 6A:
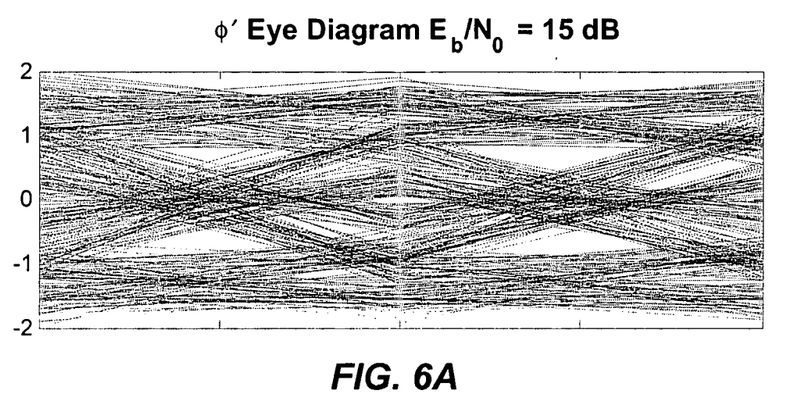
FIGS. 6A, 6B and 6C illustrate examples of full and half eye diagrams of unequalized differential GMSK decision statistics.

FIG. 5 illustrates one embodiment of the adaptive non-linear equalizer 260. The equalizer 260 can shift the corrected phase increment φ'[i] based on the previous bit decision $b_{fsk}[i-1]$ to reduce the probability of error using knowledge of the GFSK differential phase trellis. It is apparent from the unequalized corrected phase increment φ' eye pattern shown in FIG. 6A that, without equalization, bit errors are likely to occur when the transmitter 25 transmits either one of the following: a first pattern of bits $b_{fsk}[i, i+1, i+2]=[1 -1\ 1]$ or a second pattern of bits $b_{fsk}[i, i+1, i+2]=[-1\ 1 -1]$. The first pattern of bits and the second pattern of bits result in the smallest eye opening as shown in FIG. 6A.

Figure 6B:
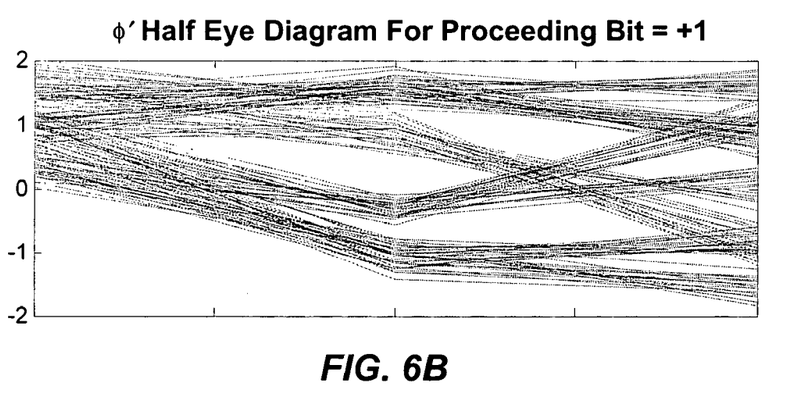
Figure 6C:
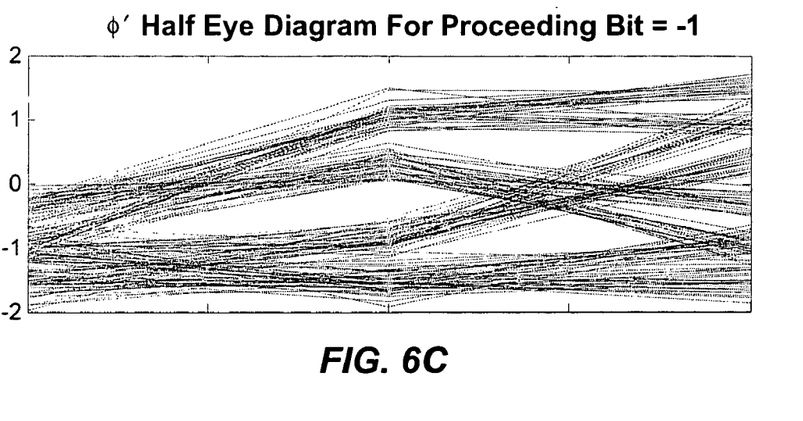

The equalizer 260 can utilize the fact that not all phase increments are allowed at every bit time. In particular, the smallest-magnitude positive phase increment can never occur when the preceding bit was a positive one (1), as shown in FIG. 6B. Similarly, the smallest-magnitude negative phase increment can never occur when the preceding bit was a negative one (−1), as shown in FIG. 6C. Accordingly, by shifting the decision statistic y[i] by shift γ at every bit instant to re-center the four known possible phase increments φ about the fixed decision threshold, the equalizer 260 opens the eye and reduces the error rate. The magnitude of the shift γ is adapted based on the estimates of the modulation index h and the filter bandwidth BT according to a transfer function $f_{eg}$(h, BT).

As illustrated in FIG. 5, the corrected phase increment φ'[i] is a first input to a combiner 305. The output is the differential FSK decision statistic y[i], which can be sampled and sent to a delay 310, such as a 1-sample delay. The equalizer decision module 315 implements a decision rule to the differential FSK decision statistic y[i] to produce the bit $b_{fsk}$[i−1]. A gain module 320 calculates the shift (i.e., ±1) based on the preceding bit $b_{fsk}$[i−1] and the shift amplitude γ calculated by the module 325. Once calculated, the shift, which is based partly on the previous bit decision $b_{fsk}$[i−1], is subtracted from the present corrected phase increment φ'[i] by the combiner 305. As stated earlier, the output yields the differential FSK decision statistic y[i].

Figure 7:
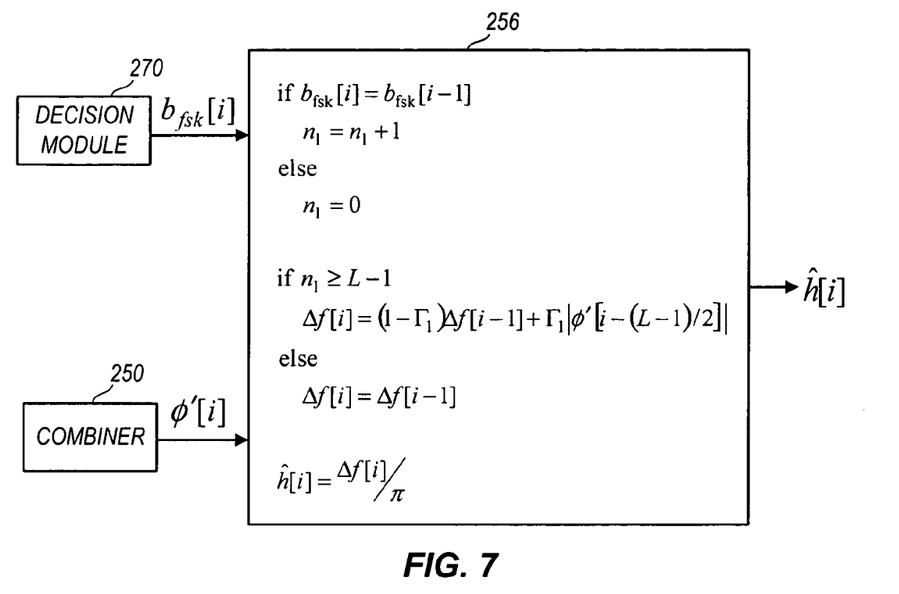
FIG. 7 is a schematic diagram of a modulation index estimation module included in the communication system of FIG. 1.

FIG. 7 illustrates one embodiment of the modulation index estimation module 256. The modulation index estimation module 256 can estimate the modulation index h by detecting bit patterns that result in full frequency shift response. In one embodiment, the pattern includes a series L of contiguous, identical bits. The series L can be the memory of the modulator's Gaussian filter in bits. Although, in principle, the series L is infinite, for a filter having a 3-dB bandwidth-bit-duration product BT≧0.2, a sliding window of L=5 is an adequate approximation. For each bit $b_{fsk}$[i] that has been preceded by at least a series of L-1 bits identical to bit $b_{fsk}$[i], the magnitude of the corrected phase increment φ' at the window's center |φ'[i−(L−1)/2]| can be used to update a smoothed estimate of the frequency deviation Δf[i] with units radians/$T_b$ where $T_b$ is the bit duration. The modulation index estimate ĥ can then be computed as ĥ=Δf[i]/π. The parameter $\Gamma_1$ can determine the bandwidth of the first-order smoothing filter.

Figure 8:
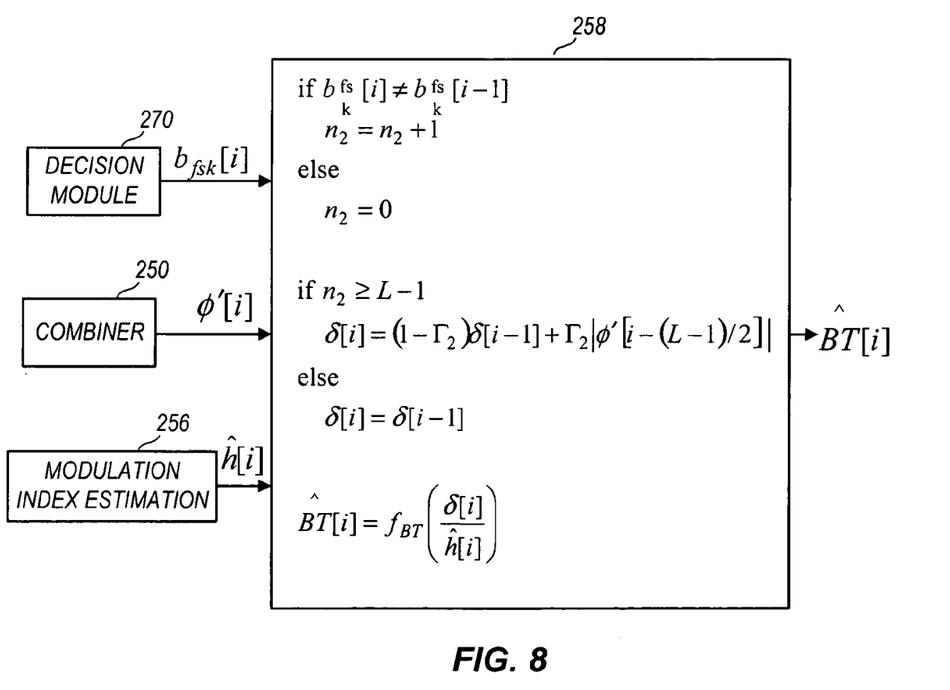
FIG. 8 is a schematic diagram of a 3-dB bandwidth-bit-duration product estimation module included in the communication system of FIG. 1.

FIG. 8 illustrates one embodiment of the 3-dB bandwidth-bit-duration estimation module 258. The 3-dB bandwidth-bit-duration estimation module 258 obtains the bandwidth-bit-duration estimate B̂T̂ by applying a transfer function $f_{BT}$(.) to the ratio δ[i]/ĥ[i] where δ[i] is a smoothed estimate of the minimum phase increment δ that occurs when a string of alternating bits is transmitted. The estimation of the minimum phase increment δ is very similar to that of the modulation index h, except that a pattern or series L including alternating bits is detected before the smoothed estimate is updated from |φ'[i−(L−1)/2]|.

Figure 9:
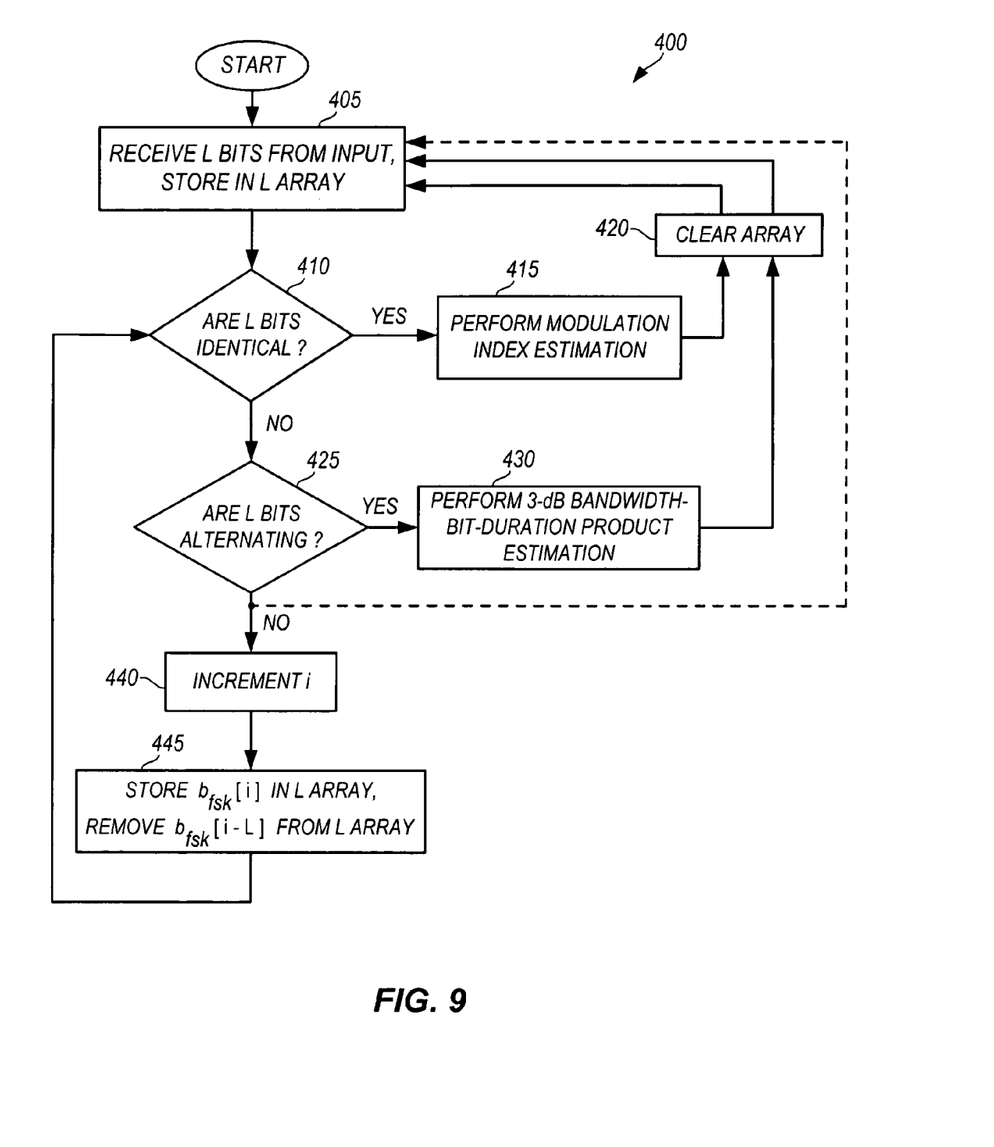
FIG. 9 is a flow chart of a method for detecting bit patterns to trigger parameter estimations according to one embodiment of the invention.

FIG. 9 is a flow chart of a method 400 of detecting the patterns which trigger the parameter estimations (e.g., modulation index estimation, 3-dB bandwidth-bit-duration estimation, etc.). The baseband receiver 35 stores (at step 405) L-number of bits from the bit stream $b_{fsk}$[i] in an array. In one embodiment, the baseband receiver 35 can store (at step 405) the first sequential L-number of bits from the bit stream $b_{fsk}$[i]. In another embodiment, the baseband receiver can implement a sorting algorithm or rule, which can store (at step 405) incoming bits into the array if the bits satisfy the algorithm. The sorting algorithm may only store the bits that are identical to the previous bits and those bits that alternate. For example, an input bit stream $b_{fsk}$[i−5, i−4, i−3, i−2, i−1, i] equals [1 1 1 0 1 0]. The sorting algorithm can begin to store bits $b_{fsk}$[i−5, i−4, i−3]=[1 1 1] in the array, because bits $b_{fsk}$[i−5, i−4, i−3] are identical. When the sorting algorithm reaches bits $b_{fsk}$[i−2, i−1, i]=[0 1 0], the algorithm can remove bits $b_{fsk}$[i−5, i−4]=[1 1] from the array and can store only the remaining four bits $b_{fsk}$[i−3, i−2, i−1, i]=[1 0 1 0], because bits $b_{fsk}$[i−3, i−2, i−1, i] are alternating.

Once L-number bits are stored (at step 405) in the array, the baseband receiver 35 can determine (at step 410) whether the L-number bits are identical. If the L-number bits are identical, then the modulation index estimation module 256 performs (at step 415) the modulation index estimation as shown and described above with respect to FIG. 7. Once the modulation index estimation module 256 performs (at step 415) the modulation index estimation, the baseband receiver 35 clears (at step 420) the array and the baseband receiver returns to step 405.

If the L-number bits are not identical (at step 410), the baseband receiver 35 can determine (at step 425) whether the L-number bits are alternating. If the L-number bits are alternating, then the 3-dB bandwidth-bit-duration estimation module 258 performs (at step 430) the 3-dB bandwidth-bit-duration estimation as shown and described above with respect to FIG. 8. Once 3-dB bandwidth-bit-duration estimation module 258 performs (at step 430) the bandwidth estimation, the baseband receiver 35 clears (at step 420) the array and the baseband receiver returns to step 405.

In one embodiment, the baseband receiver 35 returns to step 405 (as shown by the dotted lines) if the L-number bits are not alternating (at step 425). The baseband receiver returns to step 405 if the receiver 35 is implemented a sorting algorithm.

In another embodiment, the baseband receiver 35 can increment (at step 440) the index [i]. The baseband receiver 35 can also store (at step 445) the most recent bit $b_{fsk}$[i] in the array while clearing the least recent bit $b_{fsk}$[i−L] from the array. The baseband receiver 35 analyzes the array by determining (at step 410) whether the L-number of bits are identical.

In further embodiments, the baseband receiver 35 can determine if the L-number of bits are alternating prior to determining if the L-number of bits are identical. The baseband receiver 35 can also analyze the array for additional patterns or different patterns and can perform additional or different parameters estimations. In some of the embodiments, the method 400 ends when there are no more incoming bits.

It should be understood that although the above description refers to the steps shown in FIG. 9 in a particular order, that the scope of the appended claims is not to be limited to any particular order. The steps described above can be performed in various different orders and still fall within the scope of the invention.

Figure 10:
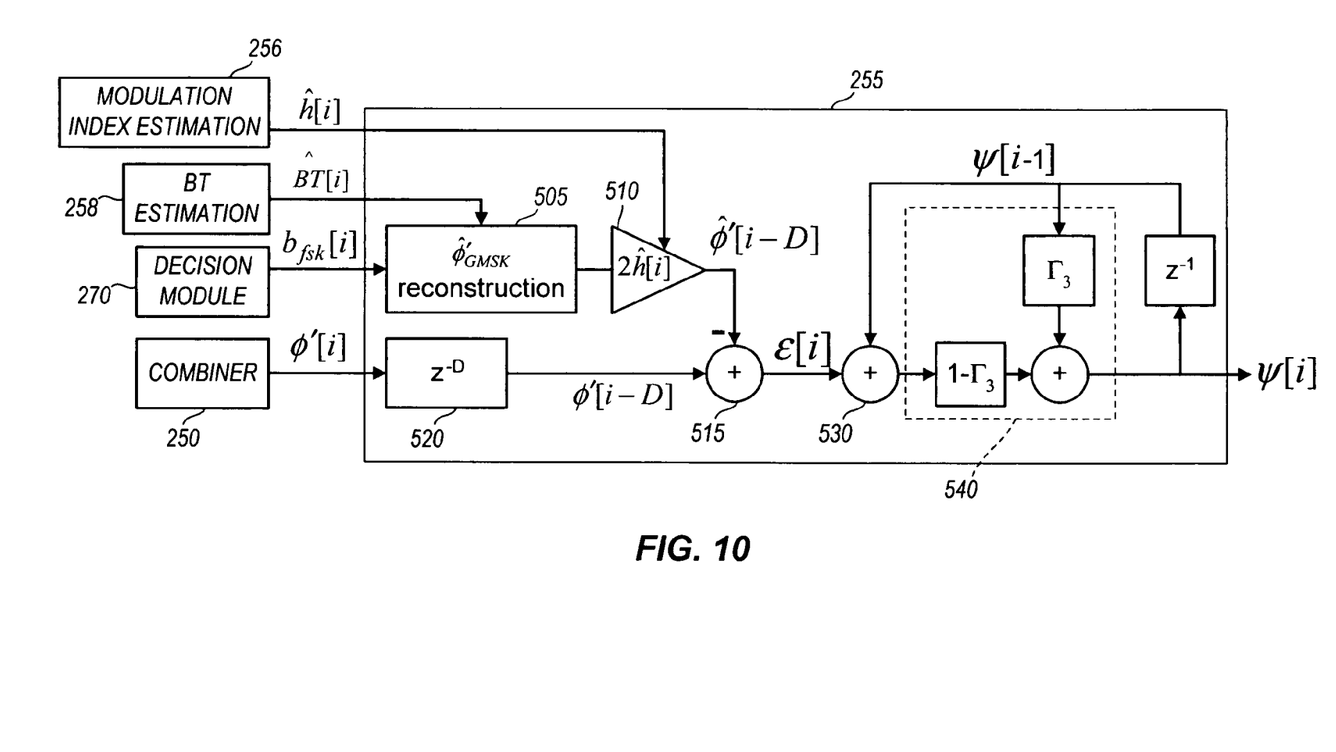
FIG. 10 is a schematic diagram of an estimation of the carrier offset estimation module included in the communication system of FIG. 1.

FIG. 10 illustrates one embodiment of the carrier offset estimation or correction module 255. The decision-directed estimation loop of module 255 can produce the predicted phase increment ψ[i] used for the carrier offset correction. A GMSK differential phase reconstruction module 505 having a delay D followed by a gain module 510 (e.g., an amplifier, having a gain 2ĥ[i]) can be used to reconstruct the expected noiseless corrected phase increment φ̂'[i], based at least partially on the demodulated bits $b_{fsk}$[i]. The expected noiseless corrected phase increment φ̂'[i−D] can be subtracted at combiner 515 from the appropriately delayed corrected phase increment φ̂'[i−D] to yield an error signal ε[i]. Before the combiner 515, the corrected phase increment φ' can pass through an n-sample delay 520. The n-sample delay 520 can have a delay D to approximately match the delay of the GMSK differential phase reconstruction module 505. The previous predicted phase increment $\psi[i-1]$ can be modified at combiner 530 by the error signal $\epsilon[i]$. The result of the combiner 530 can be smoothed using a first order filter 540 having a bandwidth set by the parameter $\Gamma_3$.

One purpose of the GMSK differential phase reconstruction module 505 is to reproduce the noiseless corrected phase increment $\psi[i]$ that would be expected for GMSK modulation with a given bandwidth BT based on a finite window of demodulated bits. One possible implementation of the GMSK differential phase reconstruction module 505 is a lookup table with each entry determined as a function of bandwidth BT. Alternatively, a symmetric linear-transversal filter or a finite impulse response ("FIR") filter with group delay $D=(L-1)/2$ may be used to approximate the ideal noiseless corrected phase increment $\phi'[i]$. For example, an FIR filter with L=3 and having coefficients $[x_1\ x_2\ x_3]$ and chosen according to the following equation works well for $BT \geq 0.2$:

$$\begin{bmatrix} 1 & 1 & 1 \\ -1 & 1 & -1 \end{bmatrix} \begin{bmatrix} x_1 \\ x_2 \\ x_3 \end{bmatrix} = \begin{bmatrix} \pi/2 \\ F_{BT}^{-1}(\hat{B}T)/2 \end{bmatrix}$$

and, $x_1 = x_3$.

As shown in FIG. 4, the baseband receiver 35 includes a first demodulator 205 and a second demodulator 210. The first demodulator 205 can use an FSK demodulation technique and the second demodulator 210 can use an OQPSK demodulation technique. The output of the second demodulator 210 (using the OQPSK demodulation technique) can be subsequently differentially encoded by an encoder 605 to correct for the inherent differential decoding that occurs in the OQPSK demodulation process. When no bit errors occur, an output bit stream $b_{OQPSK}[i]$ from the differential encoder 605 will substantially match an output bit stream $b_{fsk}[i]$ of the first demodulator 205 (using the FSK demodulation technique).

In one embodiment, the system 20 can include a receiver 28 utilizing parallel demodulators, such as the first and second demodulators 205 and 210 (shown in FIG. 4) and an error detection module 620 (shown in FIG. 4) for detecting errors. In some embodiments, the error detection module 620 can detect errors using the error correction code ("ECC") in data packets encoded by the transmitter 25 using the packetized protocol. In some embodiments, the error detection module 620 can output the output payload data 42.

Figure 11:
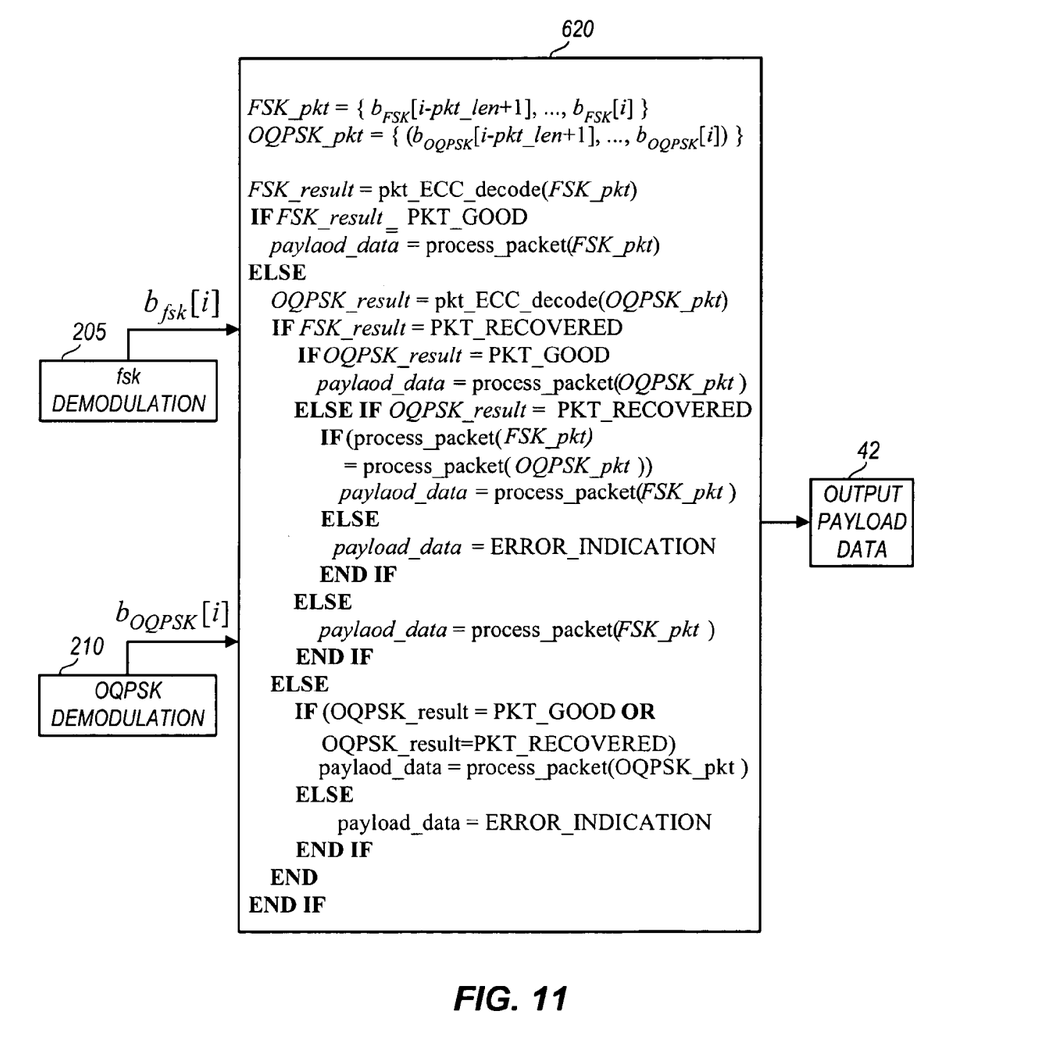
FIG. 11 is a schematic diagram of an error detection module included in the communication system of FIG. 1.

FIG. 11 illustrates one embodiment of an error detection module 620. The error detection module 620 can use the two alternate demodulator bit streams $b_{OQPSK}[i]$ and $b_{fsk}[i]$ and a rule or algorithm for choosing the correct bit stream when the demodulator bit streams $b_{OQPSK}[i]$ and $b_{fsk}[i]$ disagree.

As shown in FIG. 11, the error detection module 620 can include a packet decoding and error detection algorithm which relies on the ECC included in each packet of data. The error detection module 620 can decode the packets and rely on the ECC in the decoded packets to determine if the packet is "good" (i.e., no errors detected), "recovered" (i.e., bit errors detected and corrected) or "failed" (i.e., bit errors detected but not corrected).

In some embodiments, the performance of the receiver 28 (which utilizes the parallel demodulators 205 and 210 and the error detection module 620) may be relatively insensitive to frequency deviation, which may reduce the burden one the analog circuitry in the modulator to maintain adequate control of the modulator index h. For example, the choice of a non-MSK nominal modulation index h (e.g., a modulation index h of 0.6) in the transmitter 25 improves the worst cast system performance of the communication system 20 by biasing the distribution of the modulation indices h toward a flat region of the asymmetric receiver performance curve with only a slight increase in occupied bandwidth.

Various features and advantages of the invention are set forth in the following claims.

The invention claimed is:

1. A communication system comprising:
    a first device comprising a single modulator that modulates a first digital signal and transmits a modulated signal; and
    a second device receiving the modulated signal, the second device including
        a first demodulator receiving the modulated signal, implementing a first demodulation technique configured to demodulate of a non-minimum shift modulation indexed signal, and producing a first demodulated output;
        a second demodulator in parallel with the first demodulator, the second demodulator receiving the modulated signal, implementing a second demodulation technique configured to demodulate a minimum shift modulation indexed signal, and producing a second demodulated output and
        an error detection module performing bit error detection based on the first demodulated output and the second demodulated output.

2. The communication system as set forth in claim 1, and wherein the first demodulation technique is differential-frequency shift keying and the second demodulation technique is offset quadrature phase shift keying.

3. The communication system as set forth in claim 1, and wherein the modulated signal is modulated using a packetized protocol.

4. The communication system as set forth in claim 3, and wherein the error detection module performs bit error detection by comparing the first demodulator output with the second demodulator output on a packet-by-packet basis.

5. The communication system as set forth in claim 1, and wherein the first device implements a frequency shift keying modulation technique.

6. The communication system of claim 1 wherein the error detection module outputs a second digital signal chosen from between the first demodulated output and the second demodulated output.

7. The communication system of claim 6 wherein the error detection module chooses between the first demodulated output and the second demodulated output based on which demodulated output best represents a corresponding portion of the first digital signal.

8. The communication system of claim 7 wherein the second digital signal is substantially similar to the first digital signal.

9. A method of transferring data via a radio frequency signal, the method comprising:
    converting data into a first digital signal;
    modulating the digital signal using a packetized protocol to generate a modulated signal;
    wirelessly transferring the modulated signal;
    receiving the modulated signal;
    demodulating the modulated signal using a first demodulation technique and a second demodulation technique in parallel, the first demodulation technique producing a first demodulated signal and the second demodulation technique producing a second demodulated signal;

implementing an error detection algorithm based on the first demodulated signal and the second demodulated signal;

selecting the signal that best represents a corresponding portion of the first digital signal from between the first demodulated signal and the second demodulated signal, based on the error detection algorithm; and outputting a second digital signal based on the first demodulated signal and the second demodulated, the second digital signal being substantially identical to the first digital signal.

10. The method of claim 9, and further comprising comparing the first demodulated signal with the second demodulated signal on a packet-by-packet basis.

11. The method of claim 9 wherein the first demodulator technique is a non-minimum shift keying demodulation technique and the second demodulation technique is a minimum shift keying demodulation technique.

12. The method of claim 11 wherein the first demodulation technique is differential-frequency shift keying and the second demodulation technique is offset quadrature phase shift keying.

* * * * *